United States Patent [19]

Birchak et al.

[11] Patent Number: 4,649,343
[45] Date of Patent: Mar. 10, 1987

[54] ELECTROMAGNETIC FLUX LEAKAGE INSPECTION SYSTEM FOR FERROMAGNETIC TUBES

[75] Inventors: Robert J. Birchak, Spring, Tex.; Flora J. Harris; Amos E. Holt, both of Lynchburg, Va.

[73] Assignee: The Babcock & Wilcox Company, New Orleans, La.

[21] Appl. No.: 566,020

[22] Filed: Dec. 27, 1983

[51] Int. Cl.⁴ ..................... G01N 27/83; G01R 33/12
[52] U.S. Cl. .................................. 324/220; 324/232; 324/242; 324/262
[58] Field of Search ............................... 324/219–221, 324/232, 235, 242, 243, 228, 262

[56] References Cited

U.S. PATENT DOCUMENTS

| | | | |
|---|---|---|---|
| 2,995,701 | 8/1961 | Lloyd | 324/232 |
| 3,056,920 | 10/1962 | Herrald | 324/221 |
| 3,284,701 | 11/1966 | Kerbow | 324/221 X |
| 3,593,122 | 7/1971 | Barton | 324/220 |
| 3,597,678 | 8/1971 | Fearon | 324/220 |
| 3,913,009 | 10/1975 | Panasjuk et al. | 324/232 |
| 4,468,619 | 8/1984 | Reeves | 324/220 |
| 4,477,776 | 10/1984 | Spierer | 324/232 |

Primary Examiner—Gerard R. Strecker
Attorney, Agent, or Firm—Vytas R. Matas; Robert J. Edwards

[57] ABSTRACT

An electromagnetic inspection system for detecting, in-situ, the location and character of flaws in a relatively long, thick-walled small bore tube of a heat exchanger wherein a resultant magnetic field is induced in the wall of the tube of selected direction and magnitude by the vector addition of the magnetic fields produced by two magnetic field generators, at least one of which is carried by a scanner for traversing the tube and having an array of sensors mounted in close proximity to the wall of the tube generating a unique signal as the scanner passes a flaw in the tube.

5 Claims, 7 Drawing Figures

ELECTROMAGNETIC FLUX LEAKAGE INSPECTION SYSTEM FOR FERROMAGNETIC TUBES

This invention relates to an inspection system for determining the integrity of ferromagnetic tubes. More particularly this invention relates to an inspection system for locating and determining the characteristics of flaws in relatively long, small bore, thick-walled ferromagnetic tubes in vapor generators and other types of heat exchangers.

Before being placed in service and during operation, it is essential that the tubes in such heat exchangers be free of significant abnormalities. It is therefore an established procedure that the tubes be inspected, in-situ, prior to being placed in service and periodically thereafter so that the location and characteristics of such abnormalities, if any, can be determined and a decision made as to the seriousness thereof and the corrective action to be taken.

Typically, the in-situ inspection of a tube in a vapor generator and in other types of heat exchangers must be made from the bore of the tube as support members such as support plates, tube sheets, headers and the like, prohibit the inspection being made from the exterior of the tube.

SUMMARY OF THE INVENTION

With the foregoing in mind, it is an object of this invention to provide an electromagnetic inspection system which will, in-situ, locate and determine the characteristics of flaws in heat exchanger tubes.

A further object of this invention is to provide such a system wherein there is induced into the wall of the tube a resultant magnetic field of predetermined direction and magnitude generated by the vector addition of two magnetic fields angularly displaced one from the other.

Still another object of this invention is to provide such an inspection system wherein a rotating helical magnetic field is induced into the wall of the tubing.

A further object of this invention is to provide such a system wherein the system apparatus is located entirely within the bore of the heat exchanger tube.

Another object of this invention is to provide such an inspection system adapted to determine the location of and the characteristics of flaws in relatively long, small bore, thick-walled heat exchanger tubes wherein the cross-sectional area of the tube wall is greater than the cross-sectional area of the bore of the tube.

These and other objects would be apparent from the following description when considered in connection with the drawings, in which:

IN THE DRAWINGS

Figure 5A:
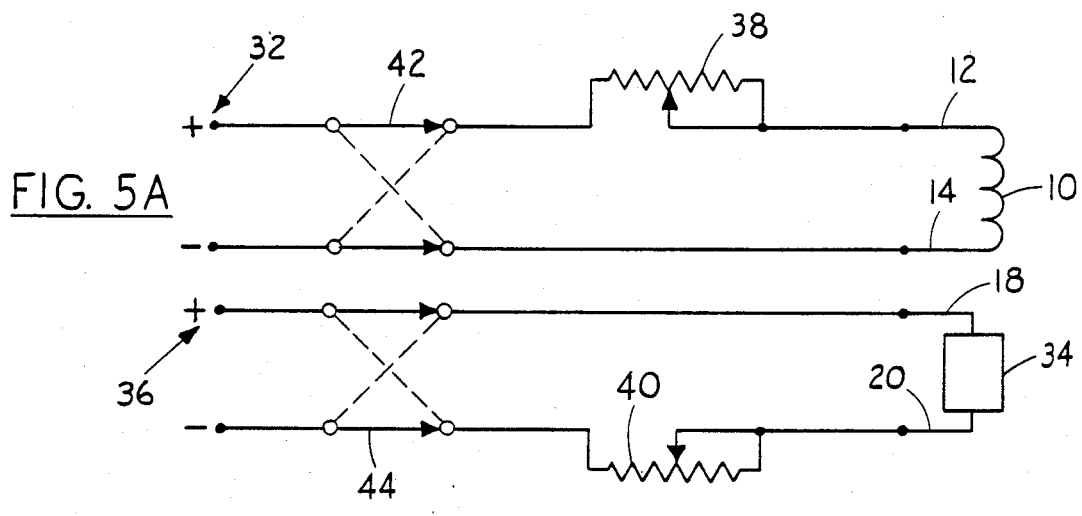
Figure 5B:
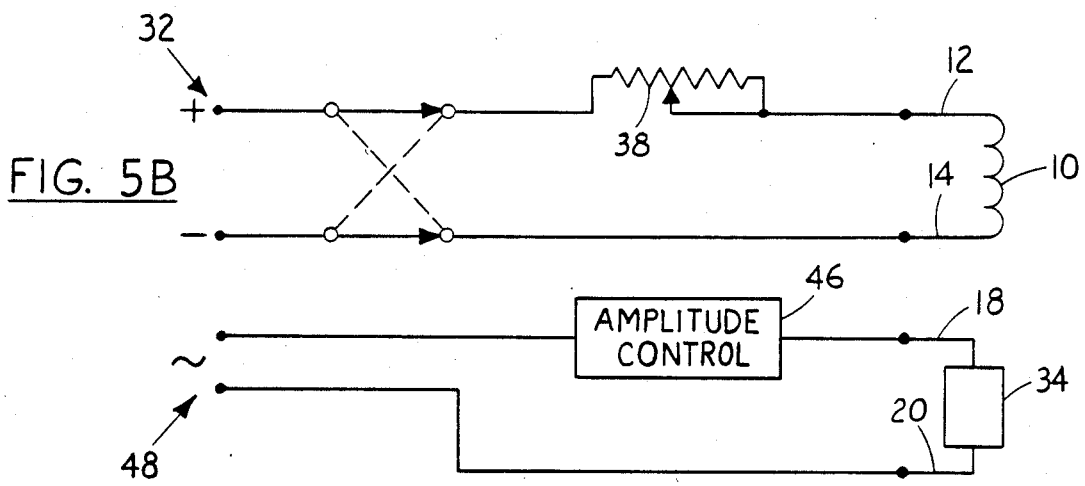
Figure 5C:
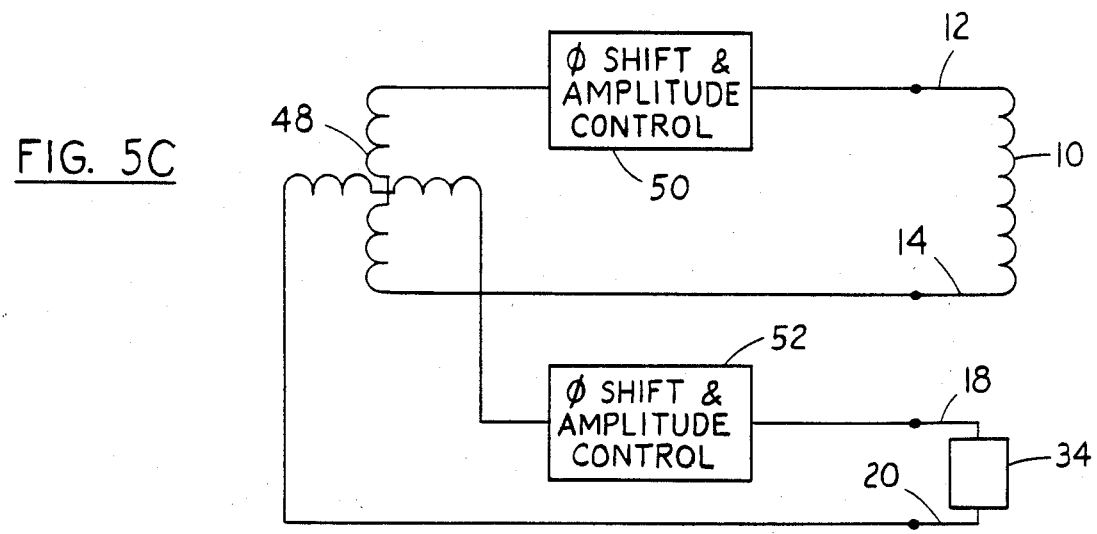

FIGS. 5A, 5B, and 5C are elementary one-line diagrams of typical circuits which may be employed in the inspection system of this invention.

DETAILED DESCRIPTION

Figure 1:
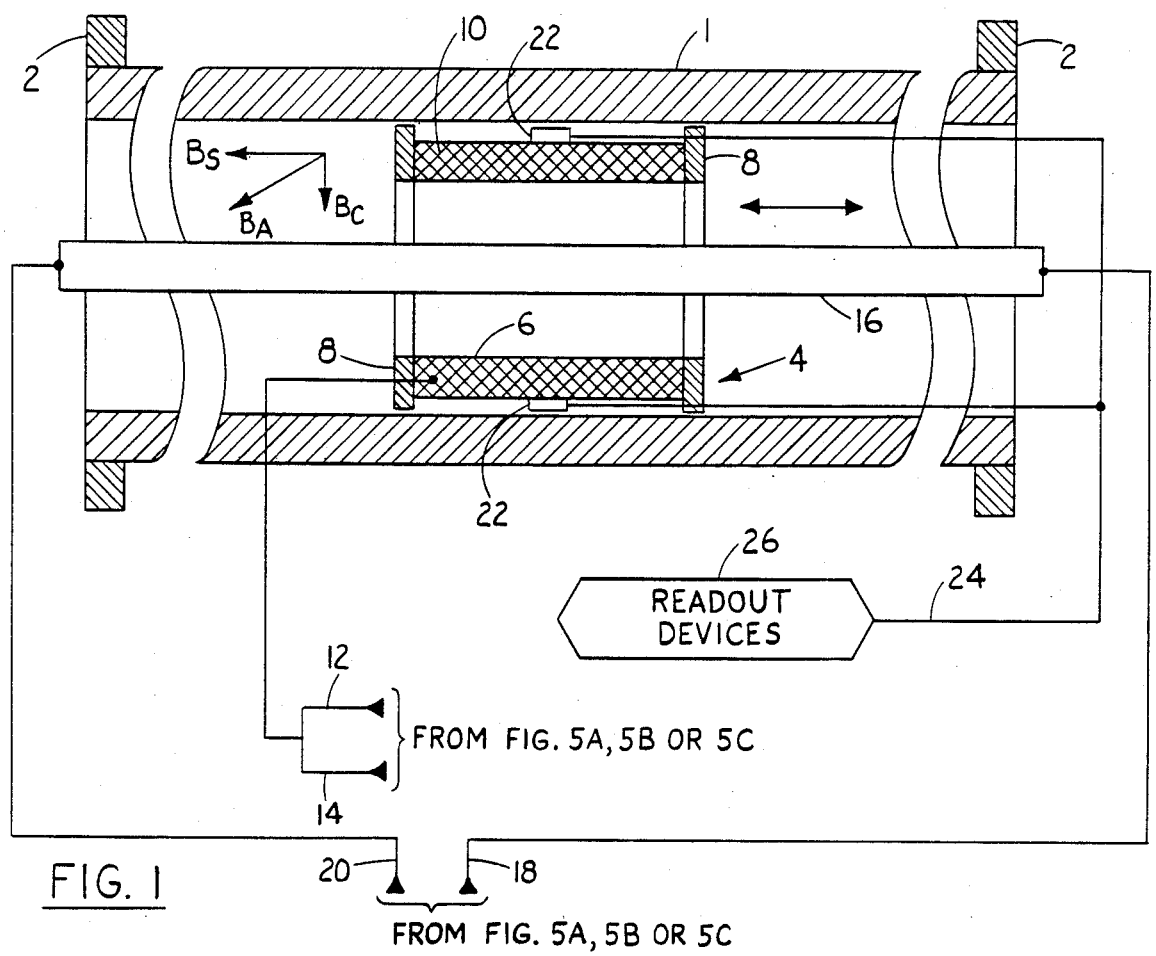
FIG. 1 is a schematic illustration of the inspection system of this invention as applied to the in-situ inspection of a typical relatively long, small bore, thick-walled heat exchanger tube.

Referring now to the drawings wherein like reference characters designate like or corresponding parts throughout the several views, there is shown in FIG. 1 a fragment of a typical relatively long, small bore, thick-walled heat exchanger tube 1 which is held in fixed position by means such as support plates 2. Shown within the bore of the tube 1 is a scanner generally indicated at 4 adapted to be drawn through the tube 1. Various arrangements are known for drawing a scanner through a tube, one such arrangement adapted to the scanning of tubes in a vapor generator is illustrated and described in U.S. Pat. No. 4,172,492.

The scanner 4 is provided with a central cylindrical hollow core 6 and a rim 8 at either end which serves to guide the scanner 4 when drawn through the tube 1. Wound upon the core 6 is a solenoid winding 10 energized through leads 12 and 14. When energized, the winding 10 produces a magnetic field ($B_s$) parallel with the longitudinal axis of the tube 1.

Centered within the tube 1 is a rigid conductor 16 energized through leads 18 and 20. When energized, the conductor 16 produces a magnetic field ($B_c$) normal to the longitudinal axis of the tube 1. When both the solenoid winding 10 and conductor 16 are energized, there is induced into the wall of the tube 1 a resultant magnetic field ($B_a$) generated by the vector addition of fields ($B_s$) and ($B_c$). The direction, magnitude and characteristics of the resulting magnetic field ($B_a$) can be adjusted as required to meet the exigency of a specific application by adjusting the relative energizations of the solenoid winding 10 and conductor 16 as hereinafter explained more in detail.

Mounted around the outer circumference of the solenoid winding 10 in close proximity to the inner wall of the tube 1 is an array of sensors 22 connected by way of cabled leads 24 to selected read-out devices schematically shown at 26. So long as the tube 1 is free from defects, the resultant magnetic field ($B_a$) will have a constant configuration dependent solely upon the energizations of the solenoid winding 10 and conductor 16. When, however, the scanner 4 traverses a tube defect, the resultant magnetic field ($B_a$) will be distorted producing a leakage flux which is detected by one or more of the sensors 22.

Figure 2:
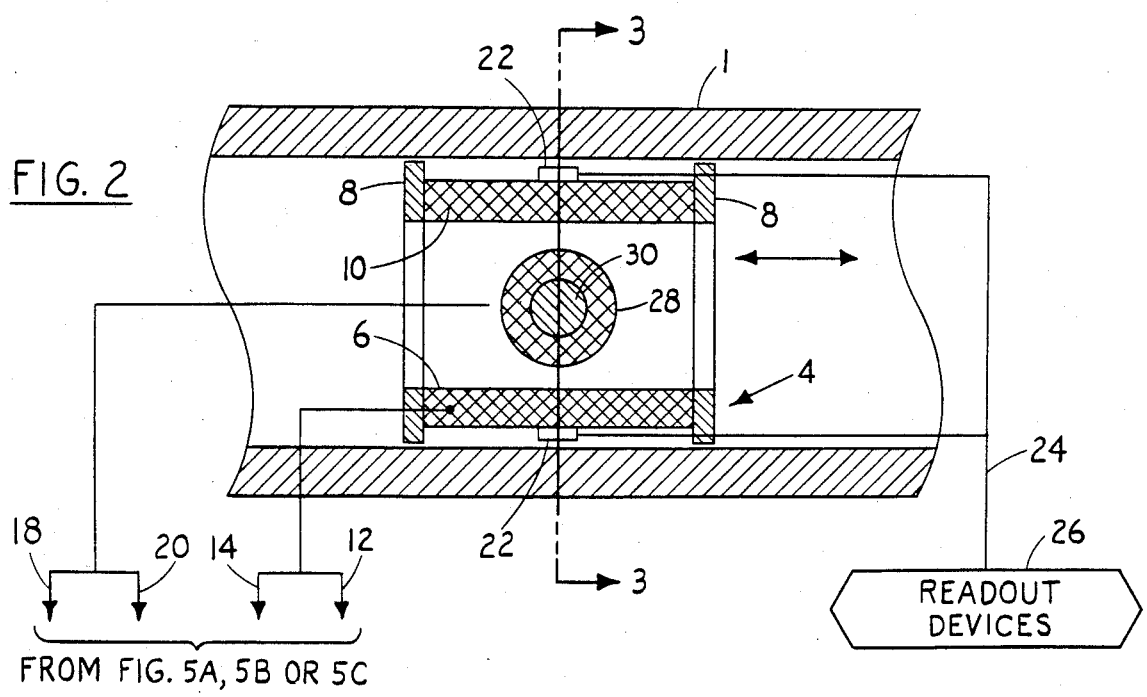
FIG. 2 illustrates a modified form of the invention.
Figure 3:
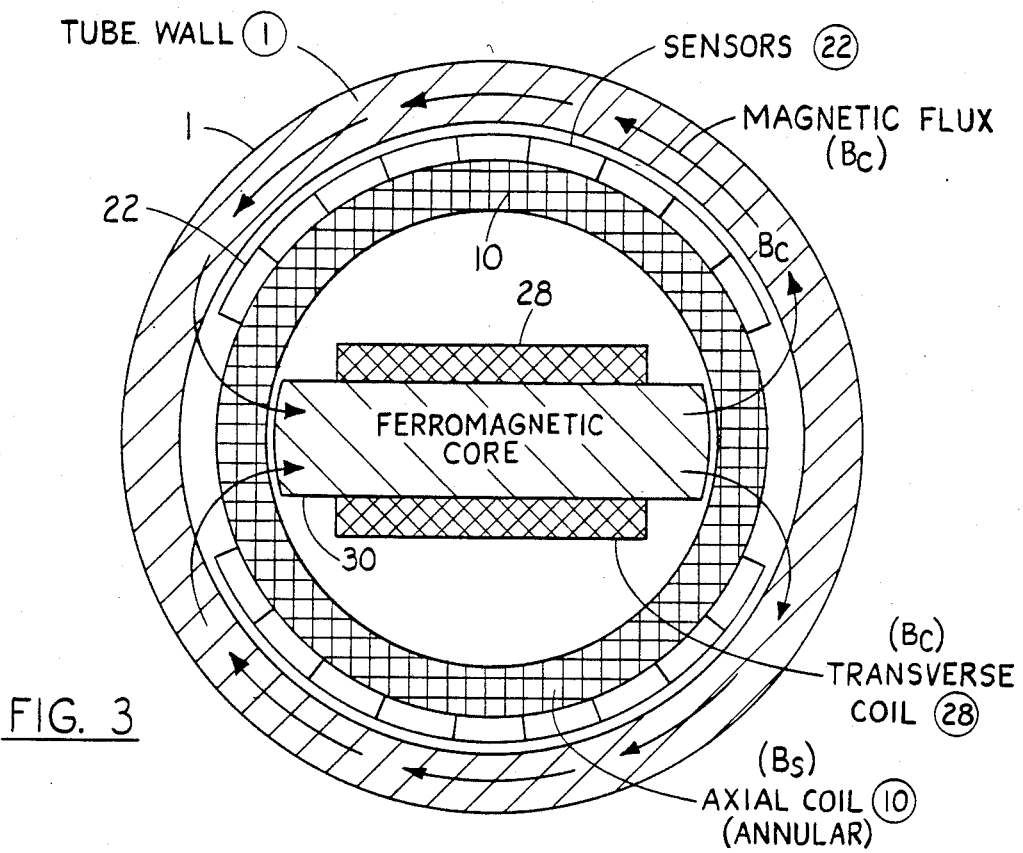
FIG. 3 is a cross-sectional view taken along the line 3—3 of FIG. 2 in the direction of the arrows.

In FIGS. 2 and 3, there is shown, respectively, a modified form of the scanner 4 in longitudinal cross-section and as viewed along the line 3—3 of FIG. 2 in the direction of the arrows. In the modified form there is disposed within the scanner 4 a transverse solenoid coil 28 wound upon a ferromagnetic core 30. The transverse solenoid coil 28, when energized, produces the flux ($B_c$).

Figure 4:
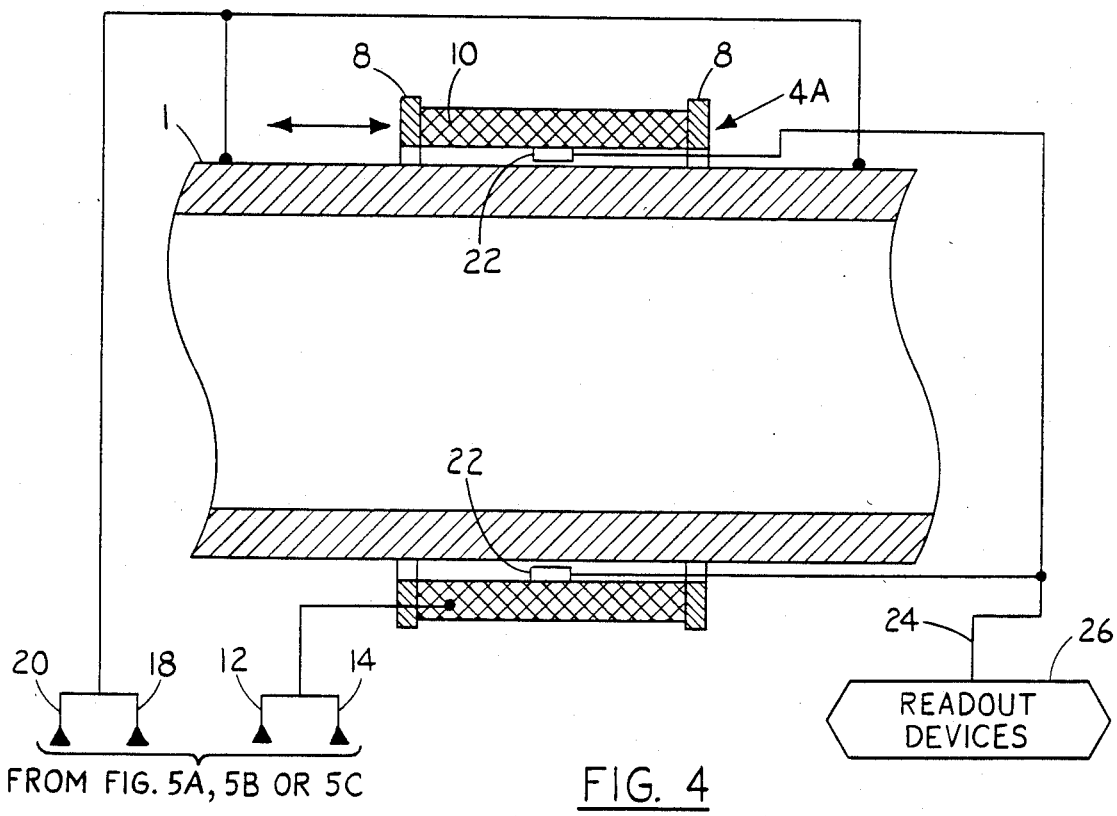
FIG. 4 illustrates a further modified form of the invention.

In FIG. 4, a further modified form of the invention is shown wherein the tube 1 is energized through leads 18 and 20, thus producing the magnetic flux ($B_c$). The solenoid winding 10 is shown as wound upon a scanner 4A surrounding the exterior of the tube 1. The winding 10 when energized through leads 12 and 14 produces the flux ($B_s$).

This invention further comprehends means for energizing the solenoid coil 10 and the conductor 16, or the solenoid coil 28, or the tube 1, as the case may be, to generate the resultant flux ($B_a$) having the characteristics required for a particular application. Thus, as shown in FIG. 5A, the solenoid coil 10 producing the flux ($B_s$) is energized from a D.C. source 32 whereas the conductor 16, or the solenoid coil 28, or the tube 1, as the case may be, schematically identified by the block 34 in FIG. 5, is energized by a D.C. source 36. Variable resistances 38, 40 provide a means whereby the resultant flux ($B_a$) can be directed through substantially 180°, by means of pole reversal switches 42, 44 to completely scan the wall of the tube 1 in a direction substantially normal to any tube wall abnormality.

In FIG. 5B, there is shown an arrangement wherein the coil 10 is energized from the D.C. source 32, whereas the block 34 is energized from an A.C. source 48 of desired frequency through an amplitude control unit diagrammatically shown at 46. As evident, the coil 10 could be energized with A.C. from source 48 through an amplitude control unit 46 and the block 34 energized from D.C. source 32.

In FIG. 5C, there is shown an arrangement wherein the coil 10 and block 34 are energized from a polyphase, source such as a two-phase source 48, to produce a rotating helical resulting flux ($B_a$) in the wall of the tube 1. There may be included in the circuits to the coil 10 and block 34, if required, phase shift and amplitude control units 50 and 52 to obtain a resultant flux ($B_a$) of desired characteristics.

We claim:

1. Apparatus for inspecting, in-situ, a heat exchanger tube, comprising:
   (a) means for inducing into the wall of a tube a resultant magnetic field produced by the vectorial addition of a first and a second magnetic field, said means including:
      (i) a scanner for traversing the tube having a hollow cylindrical body, said hollow cylindrical body being provided with an outwardly protruding rim at either end extending toward said tube to guide said scanner when scanning the tube from the bore of the tube;
      (ii) a first solenoid coil, carried by said body in close proximity to the wall of the tube, suitable for being energized by a first electrical source to generate said first magnetic field;
      (iii) a second solenoid coil, suitable for being energized by a second electrical source for generating said second magnetic field, said second solenoid coil disposed within and carried by said hollow cylindrical body perpendicular to said first solenoid coil; and
   (b) an array of sensors mounted on said first solenoid coil around the outer circumference thereof to be spaced away from the wall of said tube, generating output signals responsive to the leakage flux produced by a flaw in the wall of the tube.

2. Apparatus as set forth in claim 1 wherein said first and second electrical sources are out-of-phase alternating current sources such that a resultant, helical, rotating magnetic field is produced in the wall of the tube.

3. Apparatus as set forth in claim 1 wherein said first and second electrical sources are direct current sources.

4. Apparatus as set forth in claim 1 wherein one of said electrical sources is a direct current source and the other of said electrical sources is an alternating current source.

5. Apparatus for inspecting, in-situ, a heat exchanger tube, comprising:
   (a) means for inducing into the wall of a tube a resultant magnetic field produced by the vectorial addition of a first and a second magnetic field, said means including:
      (i) a scanner for transversing the tube having a hollow cylindrical body, said hollow cylindrical body being provided with an outwardly protruding rim at either end extending toward said tube to guide said scanner when scanning the tube from the bore of the tube;
      (ii) a first solenoid coil, carried by said body in close proximity to the wall of the tube, suitable for being energized by a first electrical source to generate said first magnetic field;
      (iii) a cylindrical conductor centered within said tube, suitable for being energized by a second electrical source to generate said second magnetic field; and
   (b) an array of sensors mounted on said first solenoid coil around the outer circumference thereof to be spaced away from the wall of said tube, generating output signals responsive to the leakage flux produced by a flaw in the wall of the tube.

* * * * *

UNITED STATES PATENT AND TRADEMARK OFFICE
CERTIFICATE OF CORRECTION

PATENT NO. : 4,649,343

DATED : March 10, 1987

INVENTOR(S) : James Robert Birchak, John Harris Flora and Amos E. Holt

It is certified that error appears in the above-identified patent and that said Letters Patent are hereby corrected as shown below:

On the first page of the patent, the first co-inventor's name should be corrected to read --James Robert Birchak--, and the second co-inventor's name should be corrected to read --John Harris Flora--.

Signed and Sealed this

Seventeenth Day of November, 1987

Attest:

DONALD J. QUIGG

Attesting Officer

Commissioner of Patents and Trademarks